United States Patent [19]

Taylor

[11] Patent Number: 5,604,122

[45] Date of Patent: Feb. 18, 1997

[54] IMPROVEMENTS IN OR RELATING TO DNA CLONING TECHNIQUES AND PRODUCTS FOR USE THEREWITH

[75] Inventor: Philip N. Taylor, Nr Dartford, United Kingdom

[73] Assignee: The University of Hull, Hull, United Kingdom

[21] Appl. No.: 307,713

[22] PCT Filed: Mar. 22, 1993

[86] PCT No.: PCT/GB93/00584

§ 371 Date: Nov. 14, 1994

§ 102(e) Date: Nov. 14, 1994

[87] PCT Pub. No.: WO93/19186

PCT Pub. Date: Sep. 30, 1993

[30] Foreign Application Priority Data

Mar. 21, 1992 [GB] United Kingdom .................. 9206210

[51] Int. Cl.$^6$ ............................. C12N 15/00; C07H 21/04
[52] U.S. Cl. ...................................... 435/172.3; 435/172.1; 435/183; 536/24.2; 935/23
[58] Field of Search ............................. 435/172.1, 172.3, 435/183; 536/24.2; 935/23

[56] References Cited

PUBLICATIONS

Lathe et al. Linker Tailing: Unphosphorylated linker oligonucleotides for joining DNA termini DNA vol. 3 173–182 1984.

Lathe et al. DNA enginneering: the use of enzymes, chemicals and oligonucleotides to restructure DNA sequences in vitro in: Genetic Engineering 4 Robert Williamson Ed. Academic Press London 2–56 1983.

Maniatis et al. Molecular Cloning a Laboratory Manual Cold Spring Harbor Laboratory 17–44 1982.

Life Technologies Catalog pp. 6–15, 6–17, 6–19, 6–34, and 6–25 1993.

Calleja et al. A new endonuclease recognizing the deoxynucleotide sequence CCNNGG from the cyanobacterium Synechocystis 6701 Nucleic Acids Res. vol. 13 6745–6751 1985.

Razin et al. Studies on the biological role of DNA methylation; IV. Mode of methylation of DNA in E. coli cells vol. 8 1783–1792 1980.

Dahl et al., "The Use of Genomic Libraries for the Isolation and Study of Eucaryotic Genes," *Genetic Engineering*, 2 (Williamson, ed.), Academic Press Inc., London, U.K., 1981, pp. 70–73.

Seth, "A New Method for Linker Ligation," *Chemical Abstracts*, 102 (19) Abstract 161508m, 163 (1985).

New England Biolabs Inc. Product Catalog, Beverly, MA (1990–1991), pp. 20, 42–45, 81.

*Primary Examiner*—Mindy Fleisher
*Assistant Examiner*—John S. Brusca
*Attorney, Agent, or Firm*—Leydig, Voit & Mayer, Ltd.

[57] ABSTRACT

A method of cloning foreign DNA into a DNA vector comprising ligating:

(1) a DNA vector having a single stranded DNA overhang at each end, said overhangs being mutually incompatible so as to prevent self-religation, with (2) a linear piece of foreign DNA having a single stranded DNA overhang at each end, each foreign DNA overhang being complementary to but at least one base shorter than each of the vector overhangs and being capable of base pairing along the entire length of the overhang with one of the vector overhangs, and sealing the gap by either transforming the double stranded DNA having a gap therein into a suitable bacterium or transfecting it into a suitable bacterium after packaging it into a suitable bacteriophage.

17 Claims, No Drawings

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
      ( A ) LENGTH: 13 base pairs
      ( B ) TYPE: nucleic acid
      ( C ) STRANDEDNESS: double
      ( D ) TOPOLOGY: linear ( i i i ) HYPOTHETICAL: YES ( i x ) FEATURE:
      ( A ) NAME/KEY: misc_feature
      ( B ) LOCATION: 4
      ( D ) OTHER INFORMATION: /note="5'PHOSPHATE REMOVED"

( x i ) SEQUENCE DESCRIPTION: SEQ ID NO: 1:

NNNCTCTGCA GNN          13

( 2 ) INFORMATION FOR SEQ ID NO: 2:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i i ) HYPOTHETICAL: YES ( x i ) SEQUENCE DESCRIPTION: SEQ ID NO: 2:

NNGGTACCNN          10

( 2 ) INFORMATION FOR SEQ ID NO: 3:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i i ) HYPOTHETICAL: YES ( x i ) SEQUENCE DESCRIPTION: SEQ ID NO: 3:

GGGGGAATTN GTAC          14

( 2 ) INFORMATION FOR SEQ ID NO: 4:

( i ) SEQUENCE CHARACTERISTICS:
      ( A ) LENGTH: 17 base pairs
      ( B ) TYPE: nucleic acid
      ( C ) STRANDEDNESS: both
      ( D ) TOPOLOGY: linear ( i i i ) HYPOTHETICAL: YES ( i x ) FEATURE:
                ( A ) NAME/KEY: misc_feature
                ( B ) LOCATION: 1..10
                ( D ) OTHER INFORMATION: /note="UNPAIRED NUCLEOTIDES"

( x i ) SEQUENCE DESCRIPTION: SEQ ID NO: 4:

GGGGGAATTN GTACCNN                                                                                          17

( 2 ) INFORMATION FOR SEQ ID NO: 5:

( i ) SEQUENCE CHARACTERISTICS:
                ( A ) LENGTH: 14 base pairs
                ( B ) TYPE: nucleic acid
                ( C ) STRANDEDNESS: double
                ( D ) TOPOLOGY: linear ( i i i ) HYPOTHETICAL: YES ( i x ) FEATURE:
                ( A ) NAME/KEY: misc_feature
                ( B ) LOCATION: 1
                ( D ) OTHER INFORMATION: /note="5'PHOSPHATE REMOVED"

( i x ) FEATURE:
                ( A ) NAME/KEY: misc_feature
                ( B ) LOCATION: complement (14)
                ( D ) OTHER INFORMATION: /note="5'PHOSPHATE REMOVED"

( x i ) SEQUENCE DESCRIPTION: SEQ ID NO: 5:

GGGGGAATTC CCCC                                                                                              14

( 2 ) INFORMATION FOR SEQ ID NO: 6:

( i ) SEQUENCE CHARACTERISTICS:
                ( A ) LENGTH: 11 base pairs
                ( B ) TYPE: nucleic acid
                ( C ) STRANDEDNESS: both
                ( D ) TOPOLOGY: linear ( i i i ) HYPOTHETICAL: YES ( i x ) FEATURE:
                ( A ) NAME/KEY: misc_feature
                ( B ) LOCATION: 1..9
                ( D ) OTHER INFORMATION: /note="UNPAIRED NUCLEOTIDES"

( x i ) SEQUENCE DESCRIPTION: SEQ ID NO: 6:

AATTCCCCCN N                                                                                                 11

( 2 ) INFORMATION FOR SEQ ID NO: 7:

( i ) SEQUENCE CHARACTERISTICS:
                ( A ) LENGTH: 19 base pairs
                ( B ) TYPE: nucleic acid
                ( C ) STRANDEDNESS: double
                ( D ) TOPOLOGY: linear ( i i i ) HYPOTHETICAL: YES ( i x ) FEATURE:
                ( A ) NAME/KEY: misc_feature
                ( B ) LOCATION: complement (12)
                ( D ) OTHER INFORMATION: /note="SINGLE NUCLEOTIDE GAP"

( x i ) SEQUENCE DESCRIPTION: SEQ ID NO: 7:

NNGGGGGAAT TNGTACCNN                                                                                         19

( 2 ) INFORMATION FOR SEQ ID NO: 8:

( i ) SEQUENCE CHARACTERISTICS:
                ( A ) LENGTH: 11 base pairs
                ( B ) TYPE: nucleic acid ( C ) STRANDEDNESS: both
( D ) TOPOLOGY: linear ( i i i ) HYPOTHETICAL: YES ( i x ) FEATURE:
    ( A ) NAME/KEY: misc_feature
    ( B ) LOCATION: 1..5
    ( D ) OTHER INFORMATION: /note="UNPAIRED NUCLEOTIDES"

( x i ) SEQUENCE DESCRIPTION: SEQ ID NO: 8:

NNGANCATGC N      11

( 2 ) INFORMATION FOR SEQ ID NO: 9:

( i ) SEQUENCE CHARACTERISTICS:
    ( A ) LENGTH: 13 base pairs
    ( B ) TYPE: nucleic acid
    ( C ) STRANDEDNESS: double
    ( D ) TOPOLOGY: linear ( i i i ) HYPOTHETICAL: YES ( i x ) FEATURE:
    ( A ) NAME/KEY: misc_feature
    ( B ) LOCATION: complement (7)
    ( D ) OTHER INFORMATION: /note="SINGLE NUCLEOTIDE GAP"

( x i ) SEQUENCE DESCRIPTION: SEQ ID NO: 9:

NNNNGANCAT GCN      13

( 2 ) INFORMATION FOR SEQ ID NO: 10:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i i ) HYPOTHETICAL: YES ( x i ) SEQUENCE DESCRIPTION: SEQ ID NO: 10:

NNGGTCACCN      10

( 2 ) INFORMATION FOR SEQ ID NO: 11:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i i ) HYPOTHETICAL: YES ( i x ) FEATURE:
    ( A ) NAME/KEY: misc_feature
    ( B ) LOCATION: 1..10
    ( D ) OTHER INFORMATION: /note="SEQ ID NO: 11 IS PROVIDED ON
        THE SAME VECTOR AS SEQ ID NO: 10, SEQ ID NO: 11 BEING
        POSITIONED 3'TO SEQ ID NO: 10"

( x i ) SEQUENCE DESCRIPTION: SEQ ID NO: 11:

NNGGTGACCN      10

( 2 ) INFORMATION FOR SEQ ID NO: 12:

( i ) SEQUENCE CHARACTERISTICS:
    ( A ) LENGTH: 12 base pairs
    ( B ) TYPE: nucleic acid
    ( C ) STRANDEDNESS: double
    ( D ) TOPOLOGY: linear ( i i i ) HYPOTHETICAL: YES ( i x ) FEATURE:
 ( A ) NAME/KEY: modified_base
 ( B ) LOCATION: 5
 ( D ) OTHER INFORMATION: /mod_base=OTHER
  / note="METHYLATED ADENINE"

( i x ) FEATURE:
 ( A ) NAME/KEY: misc_feature
 ( B ) LOCATION: complement (9)
 ( D ) OTHER INFORMATION: /note="5'PHOSPHATE REMOVED"

( i x ) FEATURE:
 ( A ) NAME/KEY: modified_base
 ( B ) LOCATION: complement (6)
 ( D ) OTHER INFORMATION: /mod_base=OTHER
  / note="METHYLATED ADENINE"

( x i ) SEQUENCE DESCRIPTION: SEQ ID NO: 12:

NNNGNTCACN NN                                                 12

( 2 ) INFORMATION FOR SEQ ID NO: 13:

( i ) SEQUENCE CHARACTERISTICS:
 ( A ) LENGTH: 12 base pairs
 ( B ) TYPE: nucleic acid
 ( C ) STRANDEDNESS: double
 ( D ) TOPOLOGY: linear ( i i i ) HYPOTHETICAL: YES ( i x ) FEATURE:
 ( A ) NAME/KEY: misc_feature
 ( B ) LOCATION: complement (8)
 ( D ) OTHER INFORMATION: /note="SINGLE NUCLEOTIDE GAP"

( x i ) SEQUENCE DESCRIPTION: SEQ ID NO: 13:

NNNGTGACCN NN                                                 12

( 2 ) INFORMATION FOR SEQ ID NO: 14:

( i ) SEQUENCE CHARACTERISTICS:
 ( A ) LENGTH: 10 base pairs
 ( B ) TYPE: nucleic acid
 ( C ) STRANDEDNESS: double
 ( D ) TOPOLOGY: linear ( i i i ) HYPOTHETICAL: YES ( i x ) FEATURE:
 ( A ) NAME/KEY: modified_base
 ( B ) LOCATION: 4
 ( D ) OTHER INFORMATION: /mod_base=OTHER
  / note="METHYLATED CYTOSINE"

( i x ) FEATURE:
 ( A ) NAME/KEY: modified_base
 ( B ) LOCATION: complement (6)
 ( D ) OTHER INFORMATION: /mod_base=OTHER
  / note="METHYLATED CYTOSINE"

( i x ) FEATURE:
 ( A ) NAME/KEY: misc_feature
 ( B ) LOCATION: complement (7)
 ( D ) OTHER INFORMATION: /note="5'PHOSPHATE REMOVED"

( x i ) SEQUENCE DESCRIPTION: SEQ ID NO: 14:

NNCNTGGNNN                                                   10

( 2 ) INFORMATION FOR SEQ ID NO: 15:

( i ) SEQUENCE CHARACTERISTICS:
 ( A ) LENGTH: 18 base pairs

```
            (B) TYPE: nucleic acid
            (C) STRANDEDNESS: double
            (D) TOPOLOGY: linear (iii) HYPOTHETICAL: YES (ix) FEATURE:
            (A) NAME/KEY: misc_feature
            (B) LOCATION: complement (14)
            (D) OTHER INFORMATION: /note="5'PHOSPHATE REMOVED"

(ix) FEATURE:
            (A) NAME/KEY: misc_feature
            (B) LOCATION: 1
            (D) OTHER INFORMATION: /note="5'PHOSPHATE REMOVED"

(xi) SEQUENCE DESCRIPTION: SEQ ID NO: 15:

GGGGGAATTC CCCCNNNN                                                       18

(2) INFORMATION FOR SEQ ID NO: 16:

(i) SEQUENCE CHARACTERISTICS:
            (A) LENGTH: 13 base pairs
            (B) TYPE: nucleic acid
            (C) STRANDEDNESS: both
            (D) TOPOLOGY: linear (iii) HYPOTHETICAL: YES (ix) FEATURE:
            (A) NAME/KEY: misc_feature
            (B) LOCATION: 1..9
            (D) OTHER INFORMATION: /note="UNPAIRED NUCLEOTIDES"

(xi) SEQUENCE DESCRIPTION: SEQ ID NO: 16:

AATTCCCCCN NNN                                                            13

(2) INFORMATION FOR SEQ ID NO: 17:

(i) SEQUENCE CHARACTERISTICS:
            (A) LENGTH: 12 base pairs
            (B) TYPE: nucleic acid
            (C) STRANDEDNESS: both
            (D) TOPOLOGY: linear (iii) HYPOTHETICAL: YES (ix) FEATURE:
            (A) NAME/KEY: misc_feature
            (B) LOCATION: 1..5
            (D) OTHER INFORMATION: /note="UNPAIRED NUCLEOTIDES"

(xi) SEQUENCE DESCRIPTION: SEQ ID NO: 17:

GTCACCNNNN NG                                                             12

(2) INFORMATION FOR SEQ ID NO: 18:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (iii) HYPOTHETICAL: YES (xi) SEQUENCE DESCRIPTION: SEQ ID NO: 18:

GGGGGAATTN                                                                10
```

IMPROVEMENTS IN OR RELATING TO DNA CLONING TECHNIQUES AND PRODUCTS FOR USE THEREWITH

The present invention relates to an improved method of cloning DNA into a vector, and to the products enabling the method to be conducted.

Any DNA cloning procedure has four essential parts: a method for generating DNA fragments; reactions which join foreign DNA to the vector; a means of introducing the artificial recombinant into a host in which it can replicate, and a method of selecting or screening for a clone of recipient cells that has acquired the recombinant.

This invention is concerned in particular with reactions which join foreign DNA (DNA to be cloned) to the vector. Consequently the choice of restriction endonucleases, the use of specific linkers or adaptor molecules and the choice of specific vectors is crucial.

The method, which can use novel linkers and vectors, can be applied to cloning cDNA, genomic DNA cloning, or the products of PCR reactions.

There are currently two methods of joining DNA in vitro, thereby enabling cloning; these suffer a number of drawbacks.

The first of these methods, and that used with genomic DNA and cDNA, utilizes the ability of DNA ligase to covalently join the cohesive ends produced by the action of certain restriction enzymes on DNA. With cohesive ends one strand of the DNA is longer than the other and therefore protrudes and forms an overhang of DNA.

The second, also used with genomic DNA and cDNA, utilizes the ability of DNA ligase to catalyse the formation of phophodiester bonds between DNA blunt ends.

The reaction that DNA ligase carries out on blunt or cohesive ended DNA is substantially the same, the only difference being that in the case of cohesive ends the ends to be joined are held in place prior to ligation by their inherent cohesiveness whereas this is not the case when blunt ends are to be joined.

DNA ligase is most commonly used to covalently bond a restriction endonuclease cut DNA fragment to a vector cut with the same restriction endonuclease. The problem with this method is that recircularization of both linearised vector and DNA fragments can occur.

Since the ligation reaction is often performed in dilute solutions the circularization of linear fragments is relatively favoured due to the reduced frequency of intermolecular annealing. This in turn affects the number of recombinants. The recircularization of the vector can be avoided by treating the linearised vector with alkaline phosphatase to remove the 5' terminal phosphate groups thus preventing self ligation.

A modification of the procedure for use with cDNA uses DNA ligase to add linkers to the flush ends of eDNA. Linkers are short pieces of double stranded DNA which contain one or more restriction sites for endonuclease restriction enzymes. These are ligated on to the cDNA (a reaction which proceeds at an acceptable rate because of the high concentration of linker ends compared to that of the cDNA ends). The DNA is then restricted with the corresponding enzyme which products a cohesive end on the DNA. DNA in this form can then be ligated into a vector because the cohesive ends of the foreign DNA make the ligation proceed at an acceptable rate despite the relatively low concentration of both vector and foreign DNA ends.

To prevent the enzyme used to cleave the linkers from restricting the foreign DNA prior to the addition of the linkers the foreign DNA is "methylated", this involves enzymically adding methyl groups on certain nucleotides within the enzymes recognition sequences. This will prevent the foreign DNA (cDNA) from being restricted despite it containing the recognition sequence of the enzyme. Thus when the linkers are restricted to yield a cohesive end the enzyme recognition sites within the foreign DNA are protected from restriction.

The difficulties associated with the aforementioned strategy involving linkers is that the linkers can ligate together to produce a "pseudo insert" a piece of DNA which is made up of a linker concatemer and does not contain any foreign DNA at all. Also, the ends of one piece of foreign DNA can ligate to the end of another and thus multiple inserts arise within a vector. The former problem is generally avoided by removal of unligated linkers after restriction with the appropriate enzyme. However this is not easy and causes many problems in itself. The latter problem has not been solved and although it is possible to "phosphatase" (i.e. enzymically remove the 5' terminal phosphate group) the foreign DNA to prevent self-ligation, if this is done the vector must not be phosphatased which means the vector can self-ligate. When this occurs the vector contains no foreign DNA at all.

It is an object of the present invention to overcome some of the problems arising out of the current cloning methods. These problems include:

1. A necessity to remove the linkers after their ligation to the foreign DNA. (Thus the present invention means that representative cDNA libraries can be prepared from extremely small amounts of mRNA, and without the difficult task of removing linkers after ligation).

2. A need to prevent the cDNA from circularising on itself, thus becoming unavailable for ligation into the vector, and 3. A need to remove the 5' terminal phosphate from the vector to prevent it from circularising on itself.

Throughout this specification the designations Z, X, N and E are used to denote non-specific nucleotides and their corresponding base pairing nucleotide, where applicable.

According to one aspect of the present invention there is provided a method of cloning foreign DNA into a DNA vector comprising ligating (1) a DNA vector having a single stranded DNA overhang at each end, said overhangs being mutually incompatible so as to prevent self religation; with (2) a linear piece of foreign DNA having a single stranded DNA overhang at each end, each foreign DNA overhang being complementary to but at least one base shorter than each of the vector overhangs and being capable of base pairing along the entire length of the overhang with one of the vector overhangs to produce a double stranded DNA having a gap therein, and sealing the gap by either transforming the double stranded DNA having the gap therein into a suitable bacterium or transfecting it into a suitable bacterium after packaging it into a suitable bacteriophage.

Once transformed or transfected into a suitable bacterium the bacteria's own repair system repairs the gap and the cleaved vector can be replicated.

Such a method has the advantages that the linkers do not have to be removed prior to ligation of the ligated foreign DNA and linker to the cleaved vector.

According to another aspect of the present invention there is provided a linker comprising a double stranded sequence of DNA having no terminal 5' phosphate group and which contains a restriction site which on methylation is capable of being restricted by a restriction endonuclease which cleaves specifically at a site which contains a methylated nucleotide therein.

Thus the linker can be produced containing the methylated nucleotide or may be methylated prior to use.

Alternatively the method con be performed by methylating the foreign DNA instead of the linkers.

Of course, no methylation would be necessary if both the DNA to be inserted into the cleaved vector and the vector to be cleaved are known not to contain the recognition sequence for the restriction enzyme used to cleave the linker.

Alternatively, the foreign DNA having a single stranded DNA overhang at each end which is substantially complementary to the single stranded DNA overhangs on the cleaved vector may be prepared by ligating a linker having no terminal 5' phosphate group. Once the linker is ligated on to the foreign DNA the preparation is stirred and/or warmed to a suitable temperature so that the DNA strand of the linker having no 5' phosphate disengages from the other linker DNA strand to leave the required overhang.

In one embodiment there is provided a method for cloning DNA, the method comprising the following steps:

1. cleaving a vector with an associated restriction endonuclease, 2. adding linkers, having no terminal 5' phosphate groups but containing methylated nucleotides in a methylated nucleotide requiring restriction site, to a piece of foreign DNA, to be inserted into said modified vector, and ligating the foreign DNA and linkers, 3. restricting said linkers which have been ligated on to the foreign DNA in step 2 with a second restriction endonuclease which cleaves specifically within said methylated nucleotide containing restriction site;

4. adding said restriction endonuclease cleaved DNA on to which said linkers have been ligated, produced in step 3, to said cleaved modified vector produced in step 1 and ligating, and 5. transforming or transfecting said product of step 4 into a suitable bacterium.

The vectors and linkers which are referred to in more detail hereafter are essentially utilized in specific combinations. For example a vector having two Bst EII sites is used with linkers containing a DpnI site and a vector having two Eco RII sites is used with linkers containing an ApyI site.

According to another aspect of the invention there is provided a cloning method involving a vector containing therein first and second restriction sites, which vector, when cleaved by a restriction endonuclease which cleaves specifically at said first and second restriction sites, will be cleaved to leave overhangs the nucleotide sequence of which will substantially complement a restriction endonuclease cut piece of foreign DNA on to which specially chosen linkers had been ligated prior to being restricted to leave overhangs, hereinafter referred to as pseudo-overhangs, the sequence of which is substantially complementary to said restriction endonuclease cleaved vector, the pseudo overhangs being one or more base pairs shorter than the overhangs on the cleaved vector.

The vector, if a plasmid, can be opened out, by cleaving the DNA fragment at the first and second restriction sites thereby cleaving out a portion of the vector using a restriction endonuclease which cleaves at said first and second restriction endonuclease site. After precipitation with ethanol, the small DNA fragment between the first and second restriction sites remains in solution. On restriction the first and second restriction sites must leave overhangs which will be at least one nucleotide longer than the pseudo overhang on the piece of DNA to be cloned on to which linkers have been ligated and which has then been restricted leaving a pseudo overhang on the foreign DNA. Thus the overhangs resulting from cleaving the vector must substantially complement the overhangs left on the foreign DNA on to which linkers have been added and which have then been restricted. The linker added to the foreign DNA will preferably have a methylated nucleotide therein and be cleaved to produce a pseudo overhang by a restriction enzyme specific to a restriction site having a methylated nucleotide therein.

In one embodiment the modified vector has two Bst EII restriction sites—5' GGTCACC 3' and 5' GGTGACC 3' therein. Thus when cleaved with Bst EII which cleaves at 5' G↑GTNACC 3' the vector will be left with a 3' CAGTG 5' overhang and a 5' GTGAC 3' overhang the common central G will mean that the cleaved vector will not reanneal and thereby be able to religate to itself.

In another embodiment the modified vector has two Eco RII restriction sites 5' CCAGG 3' and 5' CCTGG 3' therein. Thus when cleaved with Eco RII which cleaves at 5' CCWGG 3' (where W is either A or T) the vector will be left with a 5' CCAGG 3' overhang and a 3' GGACC 5' overhang, the common central A will mean that the cleaved vector will not reanneal and thereby be able to religate to itself.

In one embodiment, the linker will comprise a double stranded piece of DNA containing the methylated nucleotide, adenine. It will contain a restriction site capable of being restricted by a restriction endonuclease which cleaves only within a restriction site having a methylated adenine. The linker may, for example, be a double strand piece of DNA e.g.

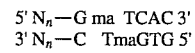

having for example the restriction site 5' GmaTC 3' within it which is cleaved by the restriction endonuclease DpnI. The enzyme will cleave between the methylated adenosine and thymine. The linker has a few additional nucleotides to one side of the restriction site such that on cleaving the linker with said restriction endonuclease (e.g. DpnI) the piece of restriction endonuclease cleaved linker which is to be ligated en to the foreign DNA will have a pseudo overhang resulting from one of the strands, (the strand containing the methylated base), falling away due to non-ligation. This pseudo overhang will substantially complement the overhang of a vector cut with a different but substantially complementary restriction endonuclease (e.g. Bst EII,) i.e. the pseudo overhang resulting from ligating and cleaving the linker to the foreign DNA must be at least one nucleotide less than the overhang of the vector. Thus in this embodiment the pseudo overhang of a linker cleaved with DpnI will be 5' TCAC 3' and the overhang of the vector will be 3' CAGTG 5'. Thus the overhang and pseudo overhang will complement one another as shown below.

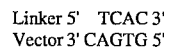

In other words the linker should read from its cleavage point 5' to 3' the complement of the 3' to 5' sticky end of the vector bearing in mind that at least the first nucleotide of the vector overhang (reading 3' to 5') is additional to the bases which make up the overhang after restriction. Thus if the vector overhang is a five nucleotide sequence e.g. 3' CAGTG 5' the linker pseudo overhang will be a four (or less) nucleotide sequence e.g. 5' TCAC 3'

In another embodiment the linker will comprise a double-stranded piece of DNA containing the methylated nucleotide cytosine.

It will contain a restriction site capable of being restricted by a restriction endonuclease which cleaves only within a restriction site having a methylated cytosine.

In this embodiment the linker is a double-stranded DNA:

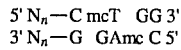

having the ApyI restriction site 5' Cmc↓TGG 3' therein. This site is cleaved by the restriction endonuclease ApyI. This enzyme cleaves between the methylated cytosine and thymine of the upper strand and between the methylated cytosine and the adenine of the lower strand to leave a cohesive end or overhang. It leaves a one base overhang

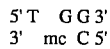

However the mcC of the lower strand (as illustrated above) will not remain in position thus yielding a three base TGG pseudo overhang. Thus 5' TGG 3' will substantially complement the overhang of a vector cut with a different restriction endonuclease, Eco RII. The overhang of the Eco RII cut vector will be 3' GGACC 5'. Thus the overhang and pseudo overhang will complement one another as shown below.

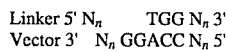

In other words the linker should read from its cleavage point 5' to 3' the complement of the 3' to 5' sticky end of the vector, bearing in mind that at least the first nucleotide of the vector overhang (reading 3' to 5') can not base pair to the linker. In this case the vector overhang will have a five nucleotide sequence

3' GGACC 5' and the linker pseudo overhang a three nucleotide sequence

5' TGG 3'.

Alternatively, according to another aspect of the present invention there is provided a method of cloning DNA which comprises:

1. Cleaving a vector with an associated restriction endonuclease;
2. Methylating a cDNA to be cloned to protect any internal restriction sites;
3. Adding linkers having a non-methylated restriction site to the cDNA to be inserted into said modified vector and ligating them;
4. Restricting said linkers which have been ligated on to the cDNA in step 3 with a second restriction endonuclease which cleaves specifically within the linker's restriction site;
5. Adding said restriction endonuclease cleaved cDNA onto which said linkers have been ligated produced in step 4 to said cleaved modified vector produced in step 1 and ligating to produce a double stranded DNA having a gap therein; and
6. Transforming or transfecting said product of step 4 into a suitable bacterium.

For example by using a gap cloning method with methylation to protect the cDNA from cleavage rather than using methylation to generate a restriction site on the linkers, different restrictions enzymes can be employed.

In one embodiment a vector employing first and second Sec I sites can be cleaved to leave incompatible overhangs. i.e. overhangs which are not capable of re-annealing under cloning conditions.

Sec I will cut the sequence

5' CCNNGG 3'
3' GGNNCC 5' leaving the respective overhangs
z=Non-specific vector nucleotide

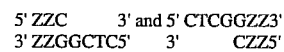

can be ligated to the cDNA and the ligated cDNA linker molecule cleaved.

Thus, if the linker is, for example,
X=Non-specific linker nucleotide

the linker can be ligated to the methylated cDNA
E=Non-specific foreign DNA nucleotide

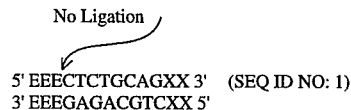

5' EEECTCTGCAGXX 3'  (SEQ ID NO: 1)
3' EEEGAGACGTCXX 5' and restricted with Pst I to give

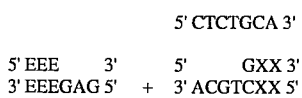

The cDNA with linker attached can then be introduced into a Sec 1 treated vector to give

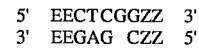

The single base pair gap being repaired after the vector with the cDNA cloned in is transfected or transformed into a bacterium.

In yet another aspect of the invention there is provided a method of cloning DNA which comprises:

1. Cleaving a vector with 3' overhang generating restriction endonuclease;
2. Ligating into the cut vector oligonucleotides which are longer than the 3' overhangs and which are capable of base pairing at one end with the overhangs, the free ends of the ligated oligonucleotides being mutually incompatible;
3. Adding linkers having no 5' phosphate groups but containing a restriction site to a piece of foreign DNA, which may have been methyloted, and ligating the foreign DNA and linkers;
4. Restricting said linkers which have been ligated on to the foreign DNA in step 3 with a second restriction endonuclease which cleaves specifically within the linker's restriction site;
5. Adding said restriction endonuclease cleaved foreign DNA on to which said linkers have been ligated as produced in step 4 to said vector as produced in step 2 and ligating to produce a double stranded DNA having a gap therein; and 6. Transforming or transfecting said product of step 4 into a suitable bacterium.

In one embodiment of this aspect of the invention the vector is cleaved with Kpn I which will cut the sequence

```
5'   ZZGGTACCZZ   3'    (SEQ ID NO: 2)
3'       CCATGG   5'
``` leaving a 4-nucleotide 3' overhang

```
5'   ZZGGTAC   3'
3'   ZZC       5'
```

Z=non specific vector nucleotide

To each end of the cut vector may be ligated an oligonucleotide having the following sequence:

```
3' CATGXTTAAGGGGG 5' (SEQ ID NO: 3)
``` resulting in an overhang at each end with the following sequence:

```
5'   ZZGGTAC                  3'
3'   ZZCCATGXTTAAGGGGG        5'   (SEQ ID NO: 4)
```

A linker having no 5' phosphate groups but having an Eco RI restriction site therein, is ligated on to the foreign DNA and then cleaved with restriction endonuclease Eco RI. Thus a linker having a sequence

```
5'   GGGGGAATTCCCCC   3'
3'   CCCCCTTAAGGGGG   5'   (SEQ ID NO: 5)
``` will, after ligation and restriction with Eco RI, result in an overhang on the foreign DNA having the sequence

```
5'   AATTCCCCXX   3'   (SEQ ID NO: 6)
3'           XX   5'
``` where X is a non-specific foreign nucleotide.

The foreign DNA with linker attached can then be introduced into the prepared vector to give

```
5'   ZZGGTAC  AATTCCCCCXX   3'
3'   ZZCCATGXTTAAGGGGGXX    5'   (SEQ ID NO: 7)
``` the single base pair gap being repaired after the vector, with the foreign DNA cloned in it, is transfected or transformed into a bacterium.

In yet another example the vector may be cleaved with Sph I which will cut the sequence

```
5'   ZGCATGCZ   3'
3'   ZCGTACGZ   5'
``` leaving a 4-nucleotide 3' overhang

```
5'   ZGCATG   3'
3'   ZC       5'
```

To each of the 3' overhangs may be ligated an oligonucleotide having the sequence 5' GTACNAGNN 3' resulting in an overhang at each end with the following sequence:

```
5'   ZGCATG              3'
3'   ZCGTACNAGNN         5'   (SEQ ID NO: 8)
```

The foreign DNA can be linked with any kind of linker provided it has a DpnI restriction site 4 base pairs from the end. Thus the linker ligated to the foreign DNA may have the following sequence:

```
5'   NNGATCNNX   3'
3'   NNCTAGNNX   5'
-Linker ———— ⎰-foreign DNA
              ⎱ no ligation
```

On restriction with DpnI the foreign DNA is left with an overhang having the sequence

```
5'   TCNNXX   3'
3'       XX   5'
```

The foreign DNA with linker attached can then be introduced into the prepared vector to give

```
5' ZGCATG   TCNNXX 3'
3' ZCGTACNAGNNXX 5'   (SEQ ID NO: 9)
``` the single base pair being repaired after the vector with the foreign DNA cloned in it is transfected or transformed into a bacterium.

Using vectors and linkers of the type referred to above, the cloning method of the present invention will now be described, by way of example only, with reference to the vectors and linkers exemplified hereinbefore, although it will be appreciated, by one skilled in the art, that the method can be modified for other vector/linker systems so long as the respective restriction sites are compatible in the manner exemplified hereinbefore.

EXAMPLE 1

Step 1

A modified pUC vector (a) (wherein 5' ZZGGTCACCZ 3' corresponds to SEQ ID NO: 10, and 5' ZZGGTGACCZ 3' corresponds to SEQ ID NO: 11) having for example two Bst EII sites cloned into the KpnI site is restricted by treatment with Bst EII. The vector is phenol extracted and the restricted vector (b) is precipitated with ethanol.

```
Vector   -5' ZZGGTCACCZ -ZZGGTGACCZ- 3'      (a)
         -3' ZZCCAGTGGZ -ZZCCACTGGZ- 5'
```

(Z = non specific vector nucleotide)

↓ Treat with BstEII

```
ENDS OF THE                                  (b)
PRECIPITATED    5' ZZG         3'   5' GTGACCZZ 3'
CLEAVED         3' ZZCCAGTG    5'        GZZ 5'
VEXTOR
```

Step 2

A fragment of DNA to be cloned has linkers ligated to its blunt ends. The linkers are unique in that they have no terminal 5' phosphate and contain a methylated nucleotide in a methylated nucleotide containing restriction site. In this specific example, the linker has a methylated adenine within the DpnI restriction site, i.e. 5' GmaTC 3'. Furthermore, it has two additional bases at the 3' end, namely 5' AC 3'. Thus on restriction with DpnI the pseudo overhang sequence 5' TCAC 3' is left. This sequence complements the end four bases 3' AGTG 5' of the Bst EII cleaved vector and this is crucial to the working of the new cloning method.

A specifically methylated DNA linker (unkinased and therefore without phosphate groups on the 5' ends) is added to the foreign cDNA (1) or, if it is not already methylated, it is methylated with dam methylase prior to addition to the DNA to be cloned (this enzyme will methylate the adenosine base within the sequence 5' GATC 3') and heated to inactivate the enzyme before it is added to the foreign DNA. The linkers are then ligated onto the foreign cDNA but as there are no 5' phosphate on the linker DNA only one strand is ligated to the foreign cDNA (2). (see below)

(X=non specific Linker DNA nucleotide)
(E=non specific Foreign DNA nucleotide)

```
LINKER 5'...XXXGma  TCAC3'    5'EEE3'                    (1)
       3'...XXXC    TmaGTG5'  3'EEE5' Foreign DNA
```

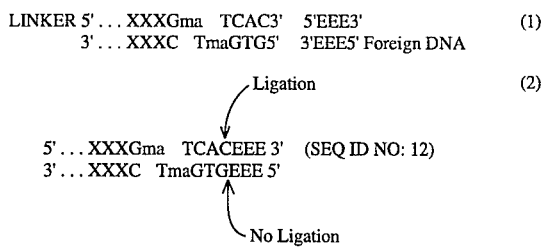

```
5'...XXXGma  TCACEEE 3'   (SEQ ID NO: 12)
3'...XXXC    TmaGTGEEE 5'
```

In other words the linker is added to the cDNA and ligated, thus the 3' hydroxyl group of the linker DNA ligates to the 5' phosphate of the cDNA. Due to the absence of a phosphate group at the 5' end of the linker DNA, the second strand does not ligate with the cDNA.

Step 3

The DNA is then cleaved with the enzyme Dpnl, this enzyme recognizes the DNA sequence 5' GmaTC 3' and cleaves it between the methylated adenosine and thymine nucleotides. It will only restrict DNA of the sequence in which the adenosine nucleotides have been methylated and therefore as none of the foreign DNA is in this form (but the linkers are) only the linkers will be restricted (3).

As the 5' end of the linker did not contain a phosphate group no ligation took place and the strand is only loosely held next to the cDNA by the hybridization to the complementary strand (3). As the strand is only loosely held in place it will break away from the complementary strand yielding a 5' TCAC 3' overhang (4).

```
5' XXXGma 3'   5'   TCACEEE 3'                 (3)
3' XXXC   T 5' 3' maGTGEEE 5'

5' XXXGma 3'   5' TCACEEEE 3'                  (4)
3' XXXC   T 5' 3'      EEEE 5'
```
maGTG Step 4

The cleaved vector (step 1) is added to the foreign DNA on to which the linkers have been ligated (step 2) and cleaved to leave a (pseudo overhang) cohesive end (step 3). The DpnI restricted linker DNA and the BstEII-restricted modified vector are ligated together. Despite the foreign DNA and the vector both having 5' overhangs with phosphate groups attached neither can self-ligate (circularize) because the ends are not complementary with each other. Only a foreign DNA (4)—and vector (5) ligation can take place. Once this ligation has occurred there is a one base "gap" in one strand of the DNA as indicated in (6).

```
5'  TCACEEE 3'                             (4)
3'      EEE 5'

5'  ZZZG      3'                           (5)
3'  ZZZCCAGTG 5'
```

Missing base does not affect ligation of the other strand

```
5'  ZZZG TCACEEE 3'   (SEQ ID NO: 13)      (6)
3'  ZZZCCAGTGEEE 5'
```

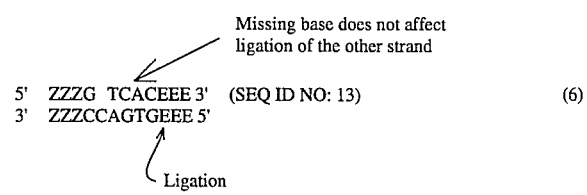
Ligation

Step 5

After transformation into a bacterium this gap is repaired during plasmid replication and the plasmid can be maintained as a stable inherited character (7),

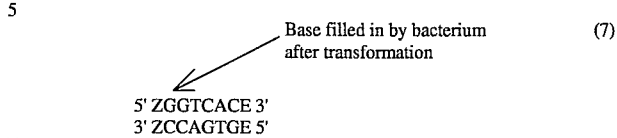
Base filled in by bacterium after transformation (7)

```
5' ZGGTCACE 3'
3' ZCCAGTGE 5'
```

EXAMPLE 2

Step 1

A modified pUC vector having for example two EcoRII sites cloned therein is restricted by treatment with EcoRII. The vector is phenol extracted and the linearised vector is precipitated with ethanol.

```
      1st site              2nd site

5' ZZCCTGGZZ...ZZCCAGGZZ 3' VECTOR
3' ZZGGACCZZ...ZZGGTCCZZ 5'
```

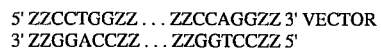
Treat with EcoRII

```
5' ZZ          3'    5' CCAGGZZ 3'    ENDS OF THE
3' ZZGGACC     5'    3'     ZZ 5'     CLEAVED
                                      PRECIPITATED
                                      VECTOR
```

Step 2

A DNA sequence to be cloned has linkers added to its blunt ends, The linkers are unique in that they have no terminal 5' phosphate but contain a methylated nucleotide in a methylated nucleotide containing restriction site.

In this specific example, the linker has a methylated cytosine within the sequence 5' CCTGG 3' thus creating an ApyI restriction site.

i.e. 5' CmcTGG 3'

On restriction with ApyI a three pseudo overhang arises. This sequence complements the end three bases 3' ACC 5' of the EcoRII cloned vector and this is crucial to the working of the new cloning method.

A specifically methylated DNA linker (Unkinased and therefore without phosphate groups on the 5' ends) is added to the foreign cDNA(1) or if it is not already methylated it is methylated with dcm methylase (this enzyme will methylate the 5' cytosine base within the sequence 5' CCAGG 3' or 5' CCTGG3') and heated to inactivate the enzyme before it is added to the foreign DNA. The linkers are then ligated on to the foreign DNA but since there are no 5' phosphate groups on the linker DNA only the one strand is ligated to the foreign DNA(2) (see below)

```
LINKER   5'  XXCmc T GG   3'  5'EEE  3'  DNA        (1)
         3'  XXG GAmc C   5' +3'EEE  5'
```

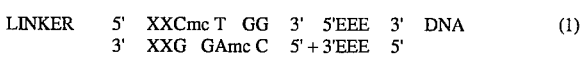
Ligation (2)

```
5'  XXCmc T GGEEE    3' (SEQ ID NO: 14)
3'  XXG GAmc CEEE    5
```

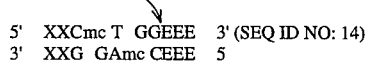
No ligation

Thus, in other words the linker is added to the DNA and ligated. Thus the 3' hydroxyl group of the linker DNA is covalently bonded to the 5' phosphate group of the foreign DNA. Due to the absence of a phosphate group at the 5' end of the linker DNA, the second strand will not ligate to the DNA.

Step 3

The DNA is then restricted with the enzyme Apyl, this enzyme recognizes the DNA sequence 5' CmcTGG 3' and cleaves it between the cytosine and thymine nucleotides and cytosine and adenine nucleotides. It will only restrict the sequence if the 3' cytosine nucleotide has previously been methylated and therefore as none of the foreign DNA is in this form (but the linkers are) only the linkers will be restricted (3).

As the 5' end of the linker did not contain a phosphate group no ligation took place and it is only loosely held next to the DNA by the hybridisation to the complementary strand (3). As the strand is only loosely held in place it will break away from the complementary strand yielding a 5' TGG 3' pseudo overhang (4).

```
5'  XXXCmc   3'      5'  T  GGEEE  3'
3'  XXXG GA  5'      3'    mcCEEE  5'   (3)

5'  XXXmc C  3'      5'  TGGEEE    3'   (4)
3'  XXX GGA  5'      3'     EEE    5'
```

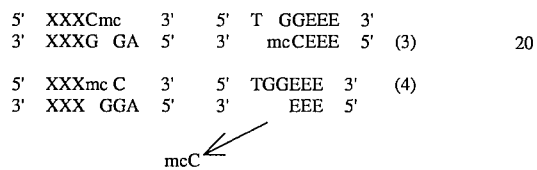

Step 4

The cleaved vector (step 1) is added to the foreign DNA on to which the linkers have been ligated (step 2) and cleaved to leave a (pseudo overhang) cohesive end (step 3). The ApyI restricted foreign DNA and the EcoRII restricted modified vector are ligated together.

Despite the foreign DNA and the vector both having 5' overhangs with phosphate groups attached neither can self ligate because the ends are not complementary with each other; only a foreign DNA (4) to vector (5) ligation can take place. Once this ligation has occurred there is a two nucleotide 'gap' on one strand of the DNA as indicated in (6)

```
VECTOR 5'  ZZZ           3' 5' TGGEEE  3'   DNA TO BE (4)
 (5)    3' ZZZGGACC      5'+3'    EEE  5'   CLONED
```

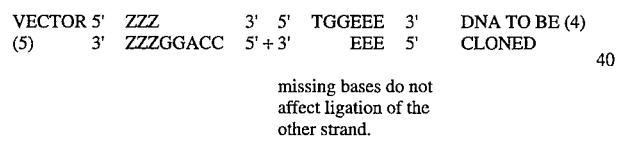

```
5'  ZZ- - TGGEE   3'
3'  ZZGGACCEE    5'      (6)
```

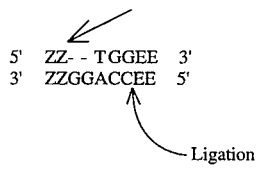

Step 5

After transformation into a bacterium the two base gap is repaired and the plasmid is maintained as a stable inherited character (7)

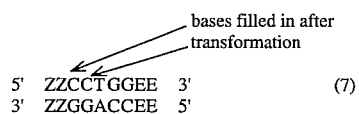

```
5' ZZCCTGGEE   3'        (7)
3' ZZGGACCEE   5'
```

EXAMPLE 3

Step 1

A modified pUC vector (a) having two Sec I sites is restricted by treatment with Sec I.

The vector is phenol extracted and the opened out vector (b) is precipiated with ethanol.

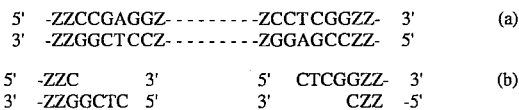

Step 2

A fragment of DNA to be cloned is methylated with Pst I methylase to protect it against restriction when treated with Pst I.

Step 3

Specially prepared linkers (c), containing a Pst I restriction site, so chosen that the linker can be used in tandem with the chosen vector, and no terminal 5' phosphate are ligated to the blunt ends of the methylated DNA (d) to be cloned.

Thus the linker contains the sequence

```
5' CTCTGCAGX 3'
3' GAGACGTCX 5'
``` which contains a Pst 1 restriction site therein; and is first ligated as shown

```
METHYLATED DNA                LINKER,
5' EEE 3'       +    5' CTCTGCAGX 3'
3' EEE 5'  (d)       3' GAGACGTCX 5'   (c)
```

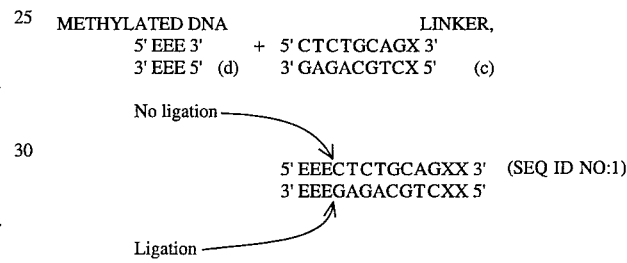

```
5' EEECTCTGCAGXX 3'   (SEQ ID NO:1)
3' EEEGAGACGTCXX 5'
```

Because the linker has no terminal 5' phosphate group, only one strand is ligated.

Step 4

The DNA into which linkers have been ligated are then cleaved with Pst I which cleaves at the sequence

```
5' CTGCAG 3'
3' GACGTC 5'
```

Since the cDNA has been specifically methylated the Pst I will only restrict the linker. Thus treatment with Pst I yields a 5' GAG 3' overhang (see below).

```
5' EEECTCTGCAGXX 3'                    (SEQ ID NO:1)
3' EEEGAGACGTCXX 5'
```

```
                          5' CTCTGCA 3'
5' EEE     3'      +  5'       GXX 3'
3' EEEGAG  5'         3' ACGTCXX 5'
```

Step 5

The cleaved vector (step 1) is added to the foreign DNA on to which the linkers have been ligated (step 3) and cleaved to leave a (pseudo overhang) cohesive end (step 4). The Pst I restricted linker DNA and the Sec 1 restricted modified vector are ligated together. Despite the foreign DNA and the vector having 5' overhangs with phosphate groups attached, neither can self-ligate (circularize) because the ends are not complementary with each other. Only foreign DNA and vector ligation can take place since due to the orientation of the central nucleotides of the Sec 1 sites in the vector a central 5' GC 3' and 3' GC 5' will exist. Once this ligation has occurred there is a one base "gap" in the strand (see below).

```
5' EEE      3'           5' CTCGGZZ- 3'
3' EEEGAG 5'          +  3'     CZZ- 5'

5'  EECTCGGZZ 5'
3'  EEGAG  CZZ 5'
```

Step 6
After transformation into a bacterium this "gap" is repaired during plasmid replication and the plasmid is maintained as a stable inherited character.

```
5'  EECTCGGZZ 3'
3'  EEGAGCCZZ 5'
```

Thus using a different combination of enzymes the same end is achieved.

EXAMPLE 4

Step 1
A λ bacteriophage vector (a) having a KpnI site is restricted by treatment with KpnI. The vector is phenol extracted and the vector (b) is precipitated with ethanol.

```
VECTOR       5' ZGGTACCZZ 3'                  (a)
             3' ZCCATGGZZ 5'                  (b)
                      │    (X = non-specific
                      │     vector nucleotide)
                      │  Treat with KpnI
                      ▼
ENDS OF THE
PRECIPITATED    5' ZZGGTAC       5'    CZZ 3'
CLEAVED VECTOR  3' ZZC           3' CATGGZZ 5'
                (i.e., having the sequence of SEQ ID NO:3)
```

Step 2
An oligonucleotide having the sequence 3' CATGXTTAAGGGGG 5' is ligated on to the cleaved vector so that the ends of the cleaved vector have the following sequence

```
5'  ZZGGTAC
3'  ZZCCATGXTTAAGGGGG  5'  (SEQ ID NO: 4)
```

The vector is passed through a chromatography column to remove the unligated oligonucleotides.

Step 3
A fragment of foreign cDNA to be cloned is methylated with EcoRI methylase to prevent the EcoRI restriction sites being subsequently cleaved. EcoRI methylase will methylate 5' GAATTC 3'. The methylated cDNA is heated to inactivate the enzyme.

A DNA linker (1) corresponding to (SEQ ID NO: 5) unkinased (and therefore without phosphate groups on the 5' ends) is added to the methylated cDNA fragment, but as there are no 5' phosphates on the linker DNA only one strand is ligated to the foreign cDNA.

```
LINKER   5' GGGGGAATTCCCCC 3'  (SEQ ID NO: 5)    (1)
         3' CCCCCTTAAGGGGG 5'

+ 5'  ZZZ  3'  cDNA
          3'  ZZZ  5'

│ LIGATION
         ▼         ligation

5' GGGGGAATTCCCCCZZZZ 3'  (SEQ ID NO: 15)
3' CCCCCTTAAGGGGGZZZZ 5' no ligation
```

Step 4
The foreign cDNA on to which linkers have been ligated is then cleaved with EcoRI. Since the cDNA has been specifically methylated the EcoRI will only restrict the linker with the result that the ends of the cDNA have a 5' AATTCCCCC 3' overhang (see below).

```
5'  AATTCCCCCZZXX  3'   (SEQ ID NO: 16)
3'            ZZXX  5'
```

Step 5
The cleaved and modified vector from step 2 is added to the foreign cDNA on to which the linkers have been ligated (step 3) and cleaved to leave a (pseudo overhang) cohesive end

```
5'  ZZGGTAC                    3'
3'  ZZCCATGXTTAAGGGGG  5'  (SEQ ID NO: 4)
                   +
5'  AATTCCCCCXX  3'   (SEQ ID NO: 6)
3'          XX  5'

5'  ZZGGTAC  AATTCCCCCXX  3'                    (3)
3'  ZZCCATGXTTAAGGGGGXX  5'   (SEQ ID NO: 7)
```

Once ligation has taken place there is a one base "gap" in the strand (3).

Step 6
After transformation into a bacteria this "gap" is repaired during plasmid replication and the plasmid is maintained as a stable inherited character.

Thus the tools required to conduct said method are an appropriate linker and an appropriate vector. In combination they can be used to conduct a cloning method with the following advantages over current cloning methods.

(a) the linkers do not have to be removed after ligation which means that representative cDNA libraries can be prepared from extremely small amounts of mRNA because the difficult task of removing the linkers after ligation is unnecessary.

(b) The cDNA cannot circularize on itself and thus become unavailable for ligation to the vector.

(c) There is no requirement to phosphatase the vector, phosphatase the cDNA or kinase the linkers.

(d) The cDNA cannot become concatemerized (form chains) and therefore the danger of multiple inserts within one vector is avoided.

(e) The cloning procedure is much faster than the previous methods and the DNA is incubated at raised temperatures for a shorter time which minimizes non-specific degradation.

(f) All of the enzymes used are standard enzymes commercially available and generally straightforward to use. (Some enzymes are difficult to use because they lose activity unless the reaction is conducted under very stringent conditions).

Although this new cloning method has been described with reference to four specific examples the method can be applied to any appropriately modified plasmid, or bacteriophage vector system, such as λ phage, when used with an appropriate linker, and should in no way be limited to the specific examples chosen to illustrate the method.

Where the vector is a bacteriophage vector the bacteriophage (which can be a linear piece of DNA) would require for example the Bst EII sites to be arranged so that the central nucleotide(s) within the recognition sequence was the same on each of the arms of the bacteriophage after restriction.

```
e.g.  5'  ZZG              GTGACCZZ  3'
      3'  ZZCCAGTG               GZZ  5'

Left arm              Right arm

5'  GTCACCZZZZZG  3' (SEQ ID NO: 17)
          3'       GZZZZZCCACTG  5'

"Stuffer" fragment.
```

In yet another aspect of the invention there is provided a DNA cloning kit which may comprise a modified DNA vector having a single stranded DNA overhang at each end, said overhangs being mutually incompatible, DNA linkers, a restriction endonuclease and a DNA ligase together with instructions for carrying out the cloning method. The DNA vector may be prepared by any of the methods hereinbefore described. The linkers used in the kit have no terminal 5' nucleotide in a methylated nucleotide containing endonuclease restriction site.

---

I claim:

1. A method of cloning foreign DNA into a DNA vector comprising: ligating respective ones of linker molecules to respective ends of a linear piece of foreign DNA and treating the foreign DNA thus formed so as to produce a single stranded overhang at each end thereof, said single stranded overhangs being formed from nucleotides derived from the ligated linkers; and ligating said foreign DNA with a single stranded overhang at each end to a DNA vector having a single stranded DNA overhang at each end, said vector overhangs being mutually incompatible so as to prevent self-religation; wherein each foreign DNA overhang is complementary to but at least one base shorter than each of the vector overhangs and is capable of base pairing along its entire length with either one of the vector overhangs to produce a double stranded DNA having a gap therein; and sealing the gap by either transforming the double stranded DNA having the gap therein into a suitable bacterium or transfecting it into a suitable bacterium after packaging it into a suitable bacteriophage.

2. A method as claimed in claim 1 wherein said linkers have no terminal 5' phosphate groups.

3. A method as claimed in claim 2 wherein said treatment to produce said foreign DNA overhangs comprises cleaving said ligated linkers with a restriction endonuclease the linkers being such that, after said cleaving, the DNA strands derived from the linkers, not covalently bound to the foreign DNA and associated with the DNA strands derived from the linkers and covalently bound to the foreign DNA, dissociate from said covalently bound strands the latter thereby forming said overhangs.

4. A method as claimed in claim 1 wherein the DNA vector having an overhang at each end is prepared by cleavage with a single restriction endonuclease at first and second restriction sites which are in opposite orientation to each other to produce single stranded DNA overhangs which are mutually incompatible.

5. A method as claimed in claim 3, wherein the DNA vector having an overhang at each end is prepared by cleavage with a single restriction endonuclease at first and second restriction sites which are in opposite orientation to each other to produce single stranded DNA overhangs which are mutually incompatible.

6. A method as claimed in claim 5, wherein the foreign DNA is methylated prior to ligating linkers to each end thereof.

7. A method as claimed in claim 5, wherein the linkers are methylated prior to ligation to the foreign DNA and said restriction endonuclease is capable of recognizing and cleaving a sequence of nucleotides which includes a methylated nucleotide.

8. A method as claimed in claim 7 wherein the first and second restriction sites have a nucleotide sequence 5' GGTCACC 3' and 5' GGTGACC 3' and are cleaved with restriction endonuclease Bst EII to generate an overhang with a nucleotide sequence 5' GTGAC 3' at each end, which overhangs are complementary to the overhangs on a piece of foreign DNA on to which linkers containing the nucleotide sequence 5' GmaTCAC 3' have been ligated and restricted with endonuclease Dpn I to generate overhangs with a nucleotide sequence 5' TCAC 3' the overhangs being one base pair shorter than the overhangs of the cleaved vector.

9. A method as claimed in claim 7 wherein the first and second restriction sites have a nucleotide sequence 5' CCTGG 3' and 5' CCAGG 3' and are cleaved with restriction endonuclease Eco RII to generate an overhang 5' CCAGG 3' at each end, which overhangs are complementary to the overhangs on a piece of foreign DNA on to which linkers containing the nucleotide sequence 5' CmcTGG 3' have been ligated and restricted with endonuclease ApyI to generate overhangs with a nucleotide sequence 5' TGG 3' the overhangs being two base pairs shorter than the overhangs of the cleaved vector.

10. A method as claimed in claim 6, wherein the first and second restriction sites have a nucleotide sequence 5' CCGAGG 3' and 5' CCTCGG 3' and are cleaved with restriction endonuclease Sec I to generate an overhang with a nucleotide sequence 5' CTCG 3' at each end, which overhangs are complementary to the overhangs on a piece of foreign DNA on to which linkers containing the nucleotide sequence 5' CTGCAGAG 3' have been ligated and restricted with endonuclease Pst I to generate overhangs with nucleotide sequence 5' GAG 3' the overhangs being one base pair shorter than the overhangs of the cleaved vector.

11. A method as claimed in claim 3, wherein the DNA vector having an overhang at each end is prepared by cleavage with a restriction endonuclease to produce 3' overhangs to each of which are ligated oligonucleotides that are longer than the overhangs and which are capable of base pairing at one end with the overhangs, the free ends of the oligonucleotides being mutually incompatible.

12. A method according to claim 11, wherein the vector is cleaved with restriction endonuclease KpnI to generate an overhang with a nucleotide sequence 3' CATG 5' at each end, to each of which overhangs is ligated an oligonucleotide having the sequence 3' CATGXTTAAGGGGG 5' (SEQ ID NO: 3) to generate an overhang with a nucleotide sequence 3' XTTAAGGGGG 5' (SEQ ID NO: 18) at each end, which overhangs are complementary to the overhangs on a piece of methylated, foreign DNA onto which linkers containing the nucleotide sequence 5' GGGGGAATTCCCCC 3' (SEQ ID NO: 5) have been ligated and restricted with endonuclease Eco RI to generate overhangs with a nucleotide sequence 5' AATTCCCCC 3', the overhangs being one base pair shorter than the overhangs on the cleaved vector.

13. A method of cloning DNA as claimed in claim 3, in which:
  (i) the vector contains first and second Bst EII sites;
  (ii) the linkers comprise a Dpn I restriction site;
  (iii) the vector is cleaved with Bst EII; and
  (iv) the ligated foreign DNA and linkers are restricted with Dpn I.

14. A method of cloning DNA as claimed in claim 3, in which:
  (i) the vector contains first and second Eco RII sites;
  (ii) the linkers comprise a ApyI restriction site;
  (iii) the vector is cleaved with Eco III; and
  (iv) the ligated foreign DNA and linkers are restricted with ApyI.

15. A method of cloning DNA as claimed in claim 3, in which:
  (i) the vector contains first and second Sec I sites;
  (ii) the linkers comprise a Pst I restriction site;
  (iii) the vector is cleaved with Sec I; and
  (iv) the ligated foreign DNA and linkers are restricted with Pst I.

16. A DNA cloning kit comprising quantities of the following components:
  (i) a DNA vector having a single stranded DNA overhang at each end, said overhangs being mutually incompatible;
  (ii) a DNA linker for ligating to a foreign DNA to be cloned;
  (iii) a restriction endonuclease for restricting said DNA linker;
  (iv) a DNA ligase;
and also comprising instructions for carrying out the cloning method of claim 1 with said components.

17. A DNA cloning kit according to claim 16 wherein the DNA linker has no 5' phosphate group and contains a methylated nucleotide in a methylated nucleotide containing endonuclease restriction site.

* * * * *